United States Patent
Nilson et al.

[11] Patent Number: 5,252,301
[45] Date of Patent: Oct. 12, 1993

[54] APPARATUS FOR THE PREPARATION OF BONE CEMENT

[75] Inventors: Thomas Nilson, Falkenberg; Jan Thorling, Falun; Staffan Smeds; Sören Jonsson, both of Linköping, all of Sweden

[73] Assignee: Cemvac System AB, Falktenberg, Sweden

[21] Appl. No.: 775,974

[22] PCT Filed: Jan. 11, 1990

[86] PCT No.: PCT/SE90/00018
§ 371 Date: Oct. 30, 1991
§ 102(e) Date: Oct. 30, 1991

[87] PCT Pub. No.: WO90/13264
PCT Pub. Date: Nov. 15, 1990

[51] Int. Cl.⁵ .................. A61B 17/56; A61L 25/00; A61F 2/46
[52] U.S. Cl. ................... 422/225; 422/224; 366/242; 366/255; 366/256; 366/267; 366/269
[58] Field of Search ............. 422/224, 225; 366/129, 366/130, 242, 255, 256, 267, 269, 332, 333

[56] References Cited

U.S. PATENT DOCUMENTS

| | | | |
|---|---|---|---|
| 2,580,316 | 12/1951 | Peebles et al. | 366/267 X |
| 4,208,133 | 6/1980 | Korte-Jungermann | 366/256 X |
| 4,676,406 | 6/1987 | Frischmann et al. | 366/256 X |
| 4,799,801 | 1/1989 | Bruning | 366/255 |
| 4,973,168 | 11/1990 | Chan | 366/255 X |

FOREIGN PATENT DOCUMENTS 61-111130  8/1986  Japan.
WO87/05492  9/1987  PCT Int'l Appl..
WO88/03811  6/1988  PCT Int'l Appl..

OTHER PUBLICATIONS

International Search Report for International Application No. PCT/SE 90/00018.

Primary Examiner—Robert J. Warden
Assistant Examiner—Stephanie Smith
Attorney, Agent, or Firm—Baker & Daniels

[57] ABSTRACT

The present invention relates to an arrangement for the manufacture of bone cement by mixing together its constituent components comprising a mixing cylinder (1) in the form of a tube with a bottom (2) and a lid (3) and inside the mixing cylinder an axially movable agitator (4). The agitator consists of a piston-like agitator disc (4a), which is perforated by channels (4a1), through which the components of the bone cement are caused to flow during the mixing procedure and an agitator rod (4b) resembling a piston rod operatively connected to the agitator disc (4a) and supported in the lid (3) in such a way that it is free to slide. The invention is characterized in that the agitator rod (4b) has an axial channel (4b1), which is closed off at the agitator disc (4a) in such a way that it is capable of being opened. The bottom (2) is so arranged, under the effect of an axial force, as to be displaced like a piston axially in the direction of the lid (3), in conjunction with which the bone cement flows out through the channel (4b1) after it has been opened.

9 Claims, 5 Drawing Sheets

APPARATUS FOR THE PREPARATION OF BONE CEMENT

The present invention relates to an arrangement for the manufacture of bone cement by mixing together its constituent components comprising a mixing cylinder in the form of a tube with a bottom and a lid and inside the mixing cylinder an axially movable agitator in the form of a piston-like agitator disc, which is perforated by channels, through which the components of the bone cement are caused to flow during the mixing procedure and an agitator rod resembling a piston rod operatively connected to the agitator disc and supported in the lid in such a way that it is free to slide.

Bone cement is used in hip-joint operations, for example. When manufacturing bone cement, for which purpose a component in the form of a powder and a liquid component require to be mixed, it is important that the mixture should be as homogeneous as possible, and that gases which occur during the mixing procedure are removed to the greatest extent possible. Any lack of homogeneity and gas inclusions have the effect of reducing the strength of the bone cement, which can result in a shorter service life for the implanted prosthesis. Furthermore, the gases which occur during manufacture are unhealthy, for which reason steps must be taken to ensure that they do not escape into the operating theatre.

The object of the present invention is to make available a preparation apparatus for bone cement, which is intended to be disposable and capable of being manufactured efficiently and at a low cost, and which also contributes to meeting the requirements stipulated above in respect of the prepared bone cement.

This object is met in that the agitator rod exhibits an axial channel, which is closed off at the agitator disc, and in that the bottom is so arranged, under the effect of an axial force, as to be displaced like a piston axially in the direction of the lid, in conjunction with which the bone cement flows out through the channel after it has been opened.

BRIEF DESCRIPTION OF THE DRAWINGS

Additional advantages of the invention can be appreciated from the accompanying dependent claims and from the following description with reference to the accompanying drawing, in which

DETAILED DESCRIPTION OF THE INVENTION

Figure 1:
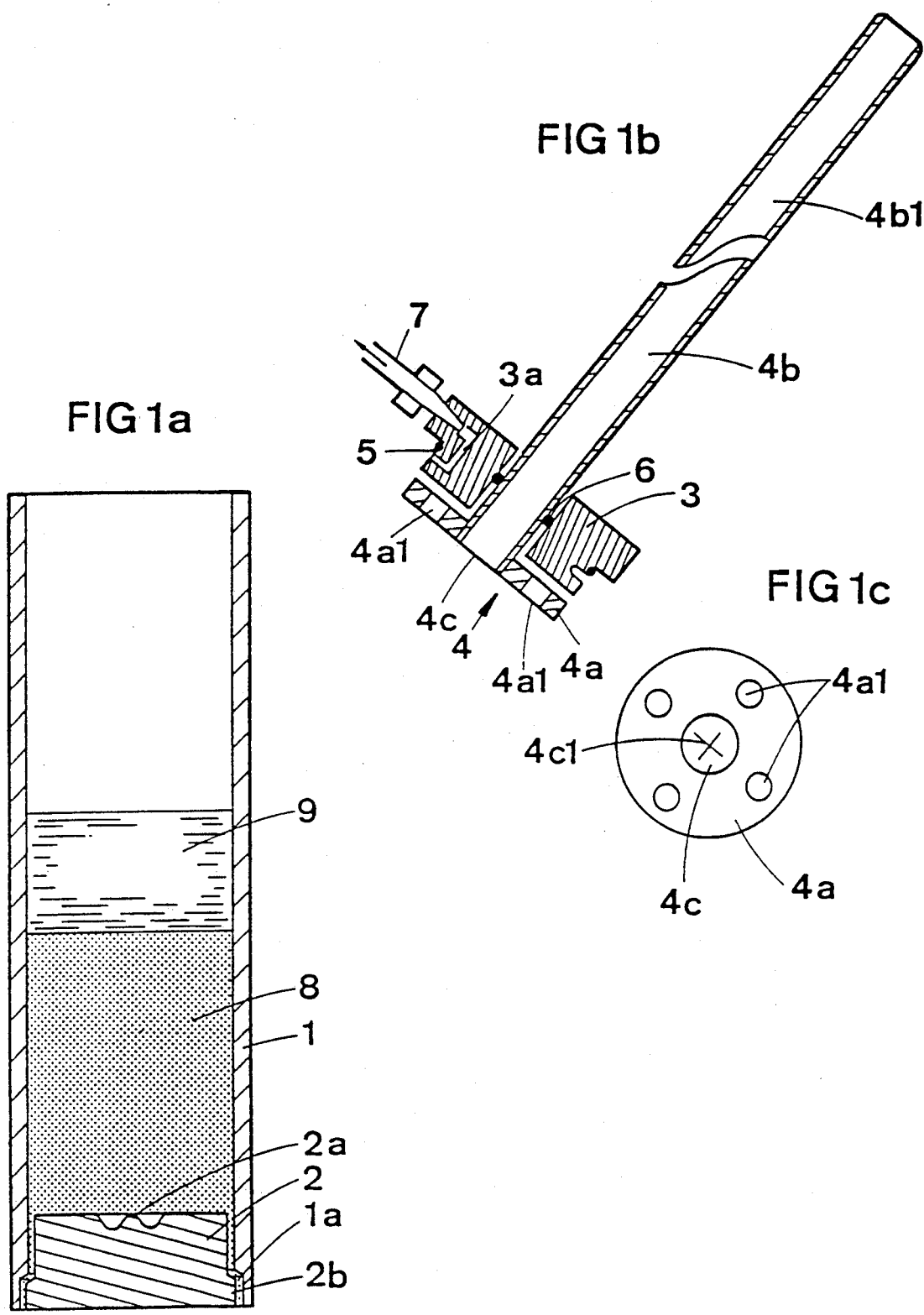
FIGS. 1a and 1b illustrate schematically in longitudinal section a mixing cylinder with a bottom and an agitator supported in a lid in such a way that it is free to slide, in accordance with a first embodiment of the preparation arrangement in accordance with the invention.
FIG. 1c illustrates an agitator disc in accordance with the invention viewed from below.

The designation 1 is used in the drawing for a mixing cylinder, and 2 for a bottom which is inserted in a sealing fashion into one end of the mixing cylinder 1. The mixing cylinder 1 is preferably made from a transparent material, and the bottom 2, which, for reasons which will become clear later, is made from a rubber-like elastic material, is formed with a projecting stud 2a facing towards the inside of the cylinder and has an annular flange-like projection 2b which engages in a corresponding groove 1a in the inner wall of the mixing cylinder 1.

The preparation arrangement in accordance with the invention also includes a lid 3 with an agitator 4 capable of axial movement therein. This comprises a piston-like agitator disc 4a and an agitator rod 4b supported in the lid 3 in such a way that it is free to slide. The lid is sealed against the inner wall of the mixing cylinder 1 and against the agitator rod 4b by means of 'O'-rings 5 and 6. The lid 3 also exhibits an evacuation channel 3a, which, via a line 7, is capable of connection to a vacuum source (not shown here), and which, when the lid 3 is fitted, discharges into the internal space of the mixing cylinder.

The agitator disc 4a is perforated by channels 4a1, through which the bone cement components are caused to flow during agitation in order to make this as effective as possible. The agitator rod 4b exhibits in accordance with the invention an axial channel 4b1, which is closed off at the end of the rod 4b which is attached to the agitator disc 4a. The closure consists of a penetrable membrane 4c. This has fractural impressions 4c1, which are illustrated in FIG. 1c.

A dot screen and the designation 8 are used in FIG. 1a to indicate a powder, and the designation 9 and a pattern of dashes to indicate a liquid, which are the components of the bone cement and have been introduced into the mixing cylinder 1 via the opening which is intended to be closed off by means of the lid 3. In the interests of clarity, these components are omitted from the other Figures.

Figure 2:
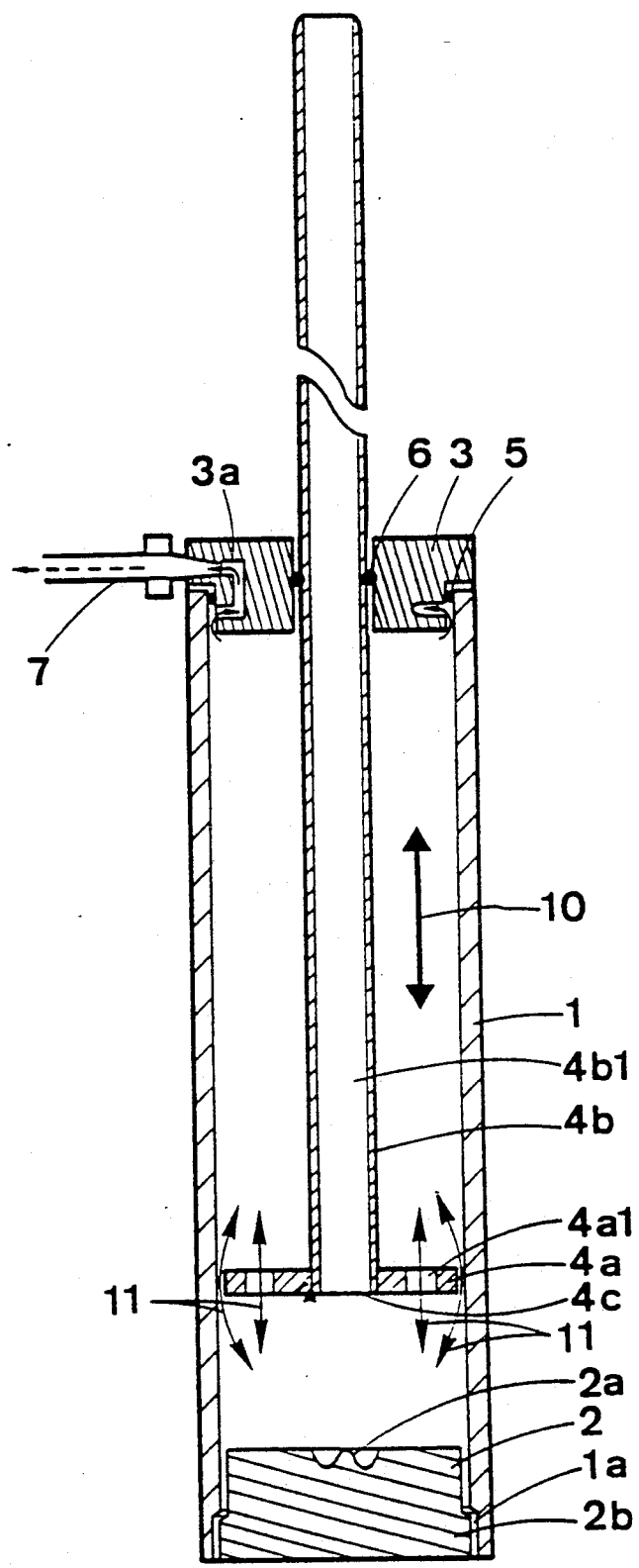
FIG. 2 is a longitudinal section through an arrangement in accordance with the aforementioned first embodiment.

The mixing procedure itself is illustrated in FIG. 2. With the help of the agitator rod 4b, the agitator disc 4a is caused to move up and down inside the mixing cylinder 1. This movement is indicated by means of a bidirectional arrow 10 in FIG. 2. Bidirectional arrows 11 are also used in the same Figure to illustrate how the components 8, 9 are caused in this way to flow through the channels 4a1 and through a space between the agitator disc 4a and the internal wall of the cylinder 1. Since the cylinder wall is transparent, a person skilled in the art can easily decide when the preparation of the bone cement is complete.

Figure 3:
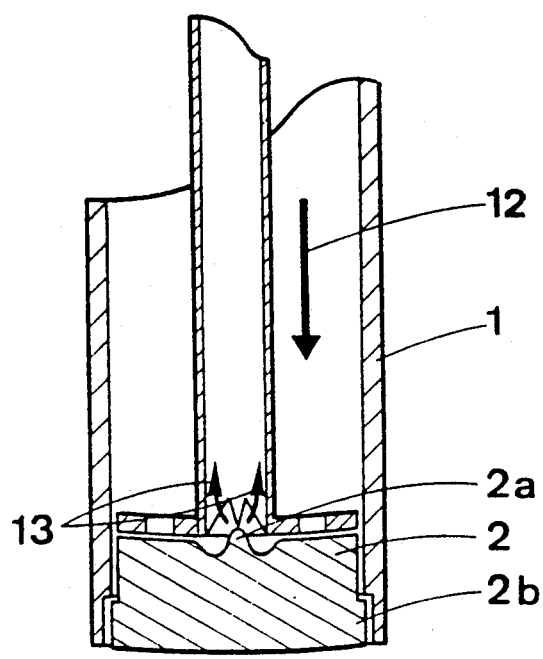
FIG. 3 illustrates in detail the penetration of a sealing membrane.

Once it has been established that the preparation is complete, the agitator 4 is moved downwards with a deliberate movement, which in FIG. 3 is illustrated by a downward-facing arrow 12, so that the agitator disc 4a contacts the bottom 2. This results in penetration of the membrane 4c by the stud 2a, causing the membrane 4c to rupture along the fractural impressions 4c1, which is illustrated by arrows 13 in FIG. 3. The agitator is then pulled to the position illustrated in FIG. 4. The channel 4b1 inside the agitator rod 4b now communicates with the space inside the mixing cylinder 1 in which the prepared bone cement is present.

Figure 4:
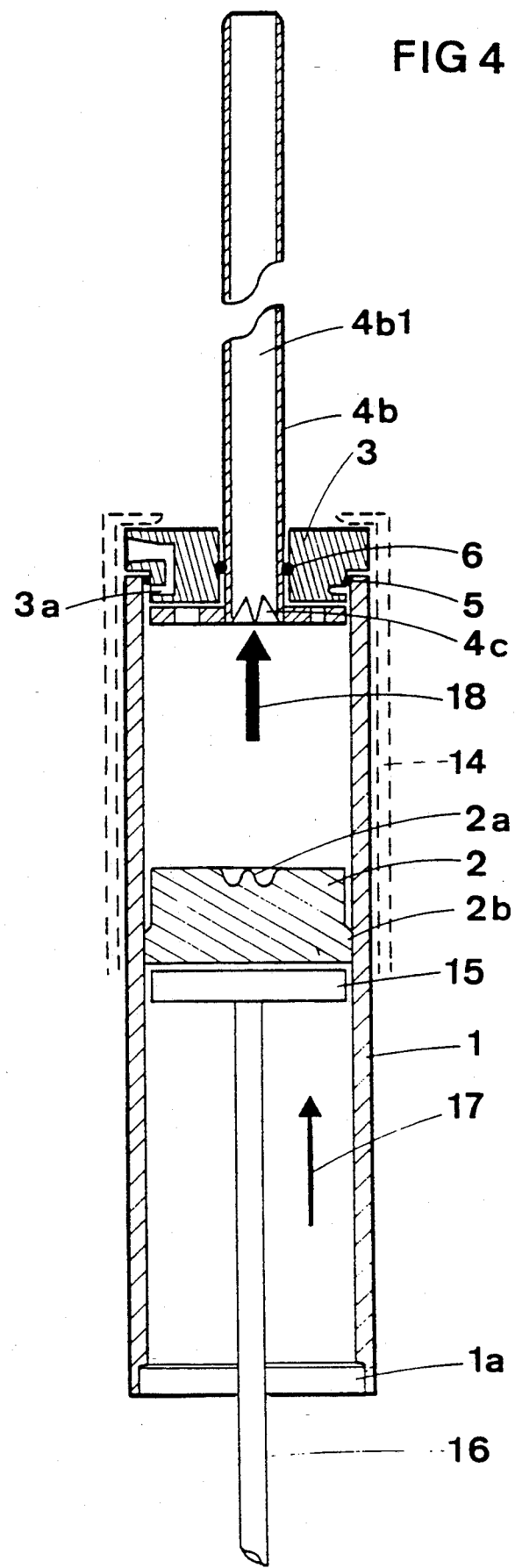
FIG. 4 illustrates how the aforementioned first embodiment of the preparation arrangement in accordance with the present invention is used as a bone cement syringe.

The preparation apparatus in accordance with the invention is now placed inside a syringe mechanism of the kind which is customarily used for the extrusion of sealing compound or similar in the form of a bead. This mechanism is indicated in FIG. 4 on the one hand as a holder part 14 marked as broken lines, in which the mixing cylinder 1 with its bottom 2, lid 3 and agitator 4 are placed, and on the other hand as a compression piston 15 with an associated compression rod 16.

When the compression piston 15 is caused to press against the bottom 2, which is illustrated by an upward-facing arrow 17, and when the compressive force has reached a sufficiently high level, the annular flange-like projection 2b will, as compression takes place, be forced out of the groove 1a and will function as a seal against the inner wall of the mixing cylinder 1. The bottom 2 now acts as a piston and forces the bone cement through the penetrated membrane 4c and via the channel 4b1 to the outside for its intended use, as shown by an arrow 18. The same reference designations are used in FIG. 5 in respect of details with the same function as, or with an analogous function to the corresponding details in the earlier Figures. This Figure illustrates the alternative embodiment of the preparation apparatus in the state in which it is supplied for use. The mixing cylinder 1 and lid 3 are manufactured in a single piece in this case, and the lid 3, like the embodiment described above, has an evacuation channel 3a and a seal 5 against the agitator rod 4b. The bottom 2 in this case is formed as an outwardly open cup with annular flange-like seals 2b in contact with the inner wall of the mixing cylinder 1.

Unlike the embodiment of an arrangement in accordance with the invention for the manufacture of bone cement described above, the embodiment in accordance with FIG. 5 has a funnel 19 removably attached to the outer end of the agitator rod 4b and a rod 20 introduced into the axial channel 4b1 of the agitator rod 4b, together with a tubular holder 21 into which the mixing cylinder 1 is introduced. The narrow opening of the funnel 19 is in close contact with the agitator rod 4b, and its purpose is to facilitate the introduction of the bone cement components into the mixing cylinder 1, for which purpose the rod 20 must have been pulled from the channel 4b1. The rod 20 is of a length such that, when introduced fully into the channel 4b 1, it reaches into the vicinity of the agitator disc 4a and is in this area executed with a seal 20a in contact with the inner wall of the channel 4b. The rod 20 with the seal 20a corresponds in its function to the membrane 4c1 described above. At its opposite end the rod 20 is executed with a draw ring 20b or similar. The mixing cylinder 1 and the piston 2 are fixed relative to the holder 21 by means of a removable cotter pin 22.

Figure 5:
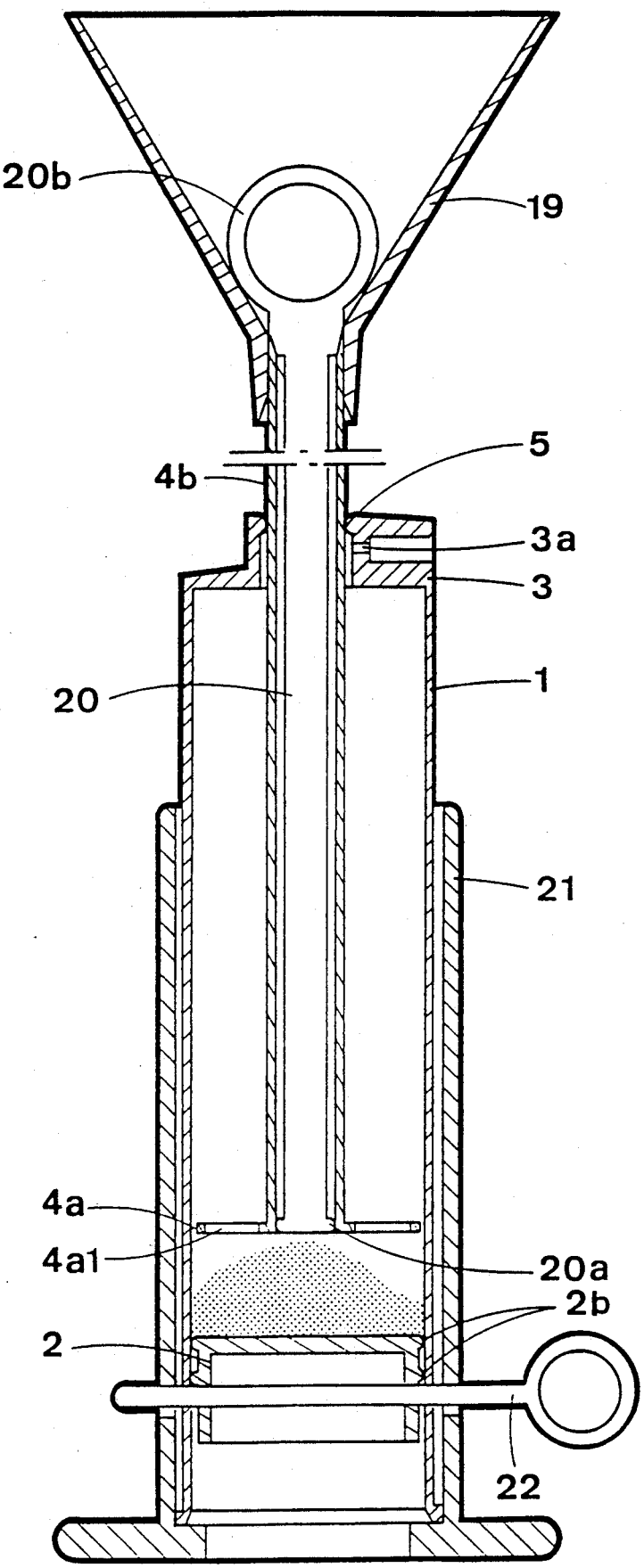
FIG. 5 is a longitudinal section through a second embodiment of the preparation arrangement in accordance with the invention.

The preparation arrangement in accordance with FIG. 5 is used as follows: The rod 20 is first removed so that the bone cement components can be introduced into the mixing cylinder 1 via the channel 4b1. The funnel 19 is then removed, and the rod 20 is introduced into the channel 4b1. The bone cement components are now mixed together, as previously described in conjunction with FIG. 2, when any gases which occur are removed via the channel 3a. During the mixing procedure the arrangement is placed in the holder 21. Once the mixing procedure is complete, the cotter pin 22 is withdrawn from its position, thereby enabling the preparation arrangement to be removed freely from its holder 21 and placed in the syringe mechanism in the manner explained in conjunction with FIG. 4. Once the cotter pin 22 has been removed, the piston 2 can be displaced axially under the effect of the compression piston 15. Once the rod 20 has been removed from the channel 4b1, bone cement can be forced out through it for the intended use.

We claim:

1. An apparatus for manufacturing bone cement by mixing a plurality of constituent components, said apparatus comprising:

a mixing cylinder having a bottom and a lid, said bottom being axially movable relative to said lid for expelling bone cement from said cylinder;

an agitator axially movably disposed in said cylinder, said agitator including a perforated member;

an elongated hollow tube connected to said agitator for guiding bone cement expelled from said cylinder, said tube axially slidably supported by said lid;

channel means in said cylinder for drawing gas from said cylinder whereby said constituent components can be drawn into said cylinder;

means for connecting said channel means to an evacuation source; and means for introducing said plurality of constituent components into said cylinder.

2. The apparatus according to claim 1 wherein said means for introducing is connected to said tube whereby said plurality of constituent components are introduced into said cylinder through said tube.

3. The apparatus according to claim 1 wherein said means for introducing comprises a funnel.

4. The apparatus according to claim 1 including closure means for said tube comprising an elongated rod having a sealing means at one end thereof for sealingly closing one end of said hollow tube whereby at least a partial vacuum can be generated in said cylinder to prevent formation of gas bubbles in said bone cement.

5. The apparatus according to claim 1 wherein said cylinder is composed of a transparent material.

6. An apparatus for manufacturing bone cement by mixing a plurality of constituent components, said apparatus comprising:

a mixing cylinder having a bottom and a lid, said bottom being axially movable relative to said lid for expelling bone cement from said cylinder;

an agitator axially movably disposed in said cylinder, said agitator including a perforated member;

an elongated hollow tube connected to said agitator for introducing constituent components into said cylinder and for guiding bone cement expelled from said cylinder, said tube axially slidably supported by said lid;

channel means in said cylinder for drawing gas from said cylinder whereby said constituent components can be drawn into said cylinder; and means for connecting said channel means to an evacuation source.

7. The apparatus according to claim 6 including funnel means connected to said tube for guiding constituent components into said tube.

8. The apparatus according to claim 1 including closure means for said tube comprising an elongated rod having a sealing means at one end thereof for sealingly closing one end of said hollow tube whereby a partial vacuum can be generated in said cylinder to prevent formation of gas bubbles in said bone cement.

9. An apparatus for manufacturing bone cement by mixing a plurality of constituent components, said apparatus comprising:
- a mixing cylinder having a bottom and a lid, said bottom being axially movable relative to said lid for expelling bone cement from said cylinder;
- a perforated agitator axially movably disposed in said cylinder;
- a rod disposed in said cylinder and having one end thereof secured to said agitator, said rod having another end thereof extending out of one end of said cylinder for axially moving said agitator;
- channel means in said cylinder for drawing air from said cylinder whereby constituent components can be drawn into said cylinder;
- means for connecting said channel means to an evacuation source; and
- means for indicating said plurality of constituent components into said cylinder.

* * * * *

UNITED STATES PATENT AND TRADEMARK OFFICE
CERTIFICATE OF CORRECTION

PATENT NO. : 5,252,301

DATED : October 12, 1993

INVENTOR(S) : Thomas Nilsson, et al

It is certified that error appears in the above-indentified patent and that said Letters Patent is hereby corrected as shown below:

On the title page, under item [19] and item [75], change "Nilson" to --Nilsson--.

Column 6, line 8, claim 9, delete "indicating" and insert therefor --introducing--.

Signed and Sealed this

Nineteenth Day of April, 1994

*Attest:*

BRUCE LEHMAN

*Attesting Officer*     *Commissioner of Patents and Trademarks*